(12) United States Patent
Ryan et al.

(10) Patent No.: US 10,722,241 B2
(45) Date of Patent: Jul. 28, 2020

(54) NITINOL OCCLUSION PLUG

(71) Applicant: Boston Scientific Scimed, Inc., Maple Grove, MN (US)

(72) Inventors: Frank Ryan, Cork (IE); Conor O'Sullivan, Cork (IE); John-Alan O'Brien, Rockmount (IR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 653 days.

(21) Appl. No.: 14/951,272

(22) Filed: Nov. 24, 2015

(65) Prior Publication Data

US 2016/0143646 A1    May 26, 2016

Related U.S. Application Data

(60) Provisional application No. 62/083,669, filed on Nov. 24, 2014.

(51) Int. Cl.
*A61B 17/12* (2006.01)
*A61B 17/00* (2006.01)

(52) U.S. Cl.
CPC .... *A61B 17/12145* (2013.01); *A61B 17/1215* (2013.01); *A61B 17/12031* (2013.01); *A61B 17/12109* (2013.01); *A61B 17/12113* (2013.01); *A61B 2017/00867* (2013.01); *A61B 2017/1205* (2013.01)

(58) Field of Classification Search
CPC ............... A61F 2/02; A61B 17/12031; A61B 17/12145; A61B 17/1215
See application file for complete search history.

(56) References Cited

U.S. PATENT DOCUMENTS

| | | | | |
|---|---|---|---|---|
| 5,382,259 A * | 1/1995 | Phelps | ............. | A61B 17/12022 604/907 |
| 5,645,558 A * | 7/1997 | Horton | ............. | A61B 17/12022 606/191 |
| 5,749,891 A * | 5/1998 | Ken | ................. | A61B 17/12022 606/200 |
| 6,187,027 B1 * | 2/2001 | Mariant | ............. | A61B 17/1215 606/151 |
| 8,795,319 B2 * | 8/2014 | Ryan | ................. | A61B 17/12031 606/200 |
| 8,870,908 B2 * | 10/2014 | Labdag | ............. | A61B 17/12022 606/200 |
| 2002/0002382 A1 | 1/2002 | Wallace et al. | | |
| 2007/0082021 A1 | 4/2007 | Bates | | |
| 2007/0142859 A1 * | 6/2007 | Buiser | ............. | A61B 17/12022 606/200 |
| 2008/0221554 A1 * | 9/2008 | O'Connor | ........ | A61B 17/12022 604/526 |

* cited by examiner

*Primary Examiner* — Julie A Szpira

(57) ABSTRACT

Occlusive plugs are provided which comprise a single elongate member that is insertable into and through a microcatheter and assumes a space-occupying shape when deployed into a vascular structure. The elongate member optionally includes one or more polymer fibers, one or more polymer sleeves to secure the polymer fibers to the elongate member, and/or a radiopaque marker band.

20 Claims, 2 Drawing Sheets

NITINOL OCCLUSION PLUG

FIELD OF THE INVENTION

Figure 1:
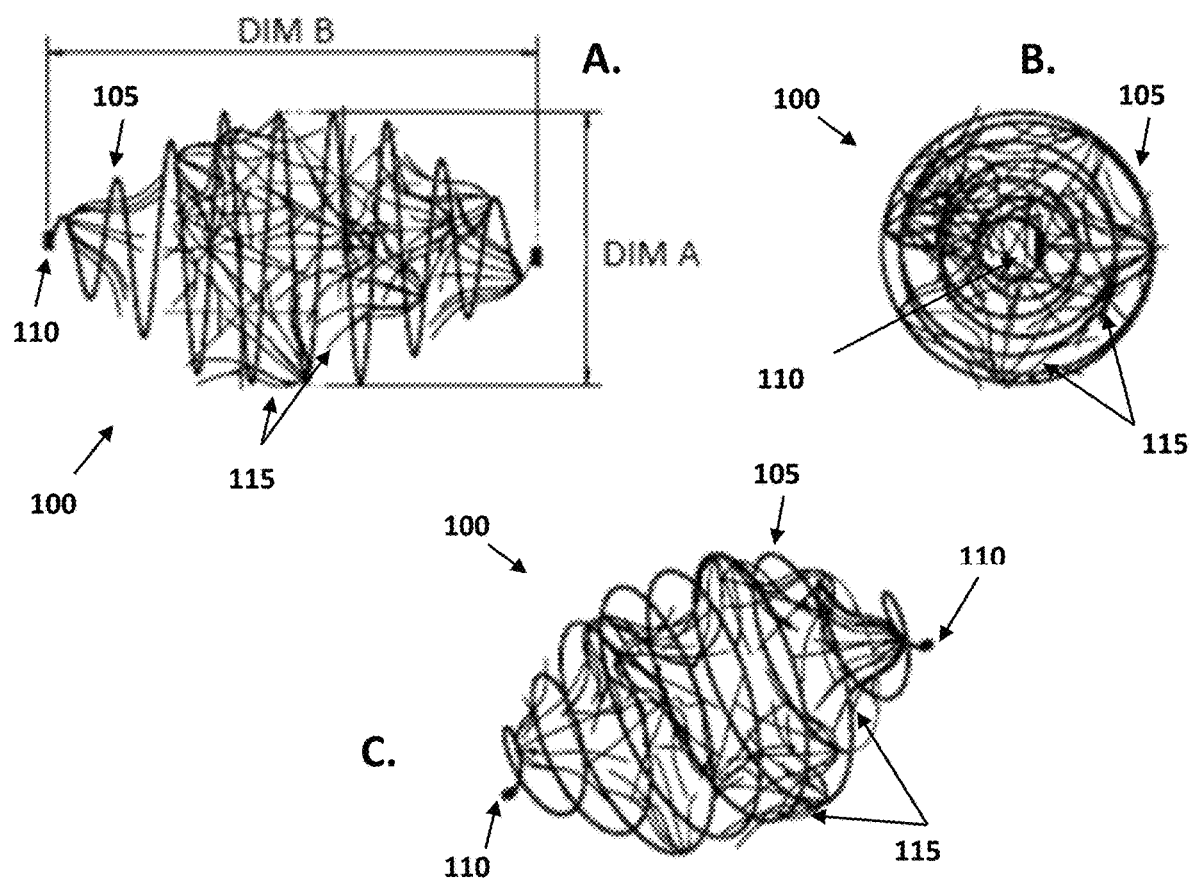

This application relates to the field of medical devices and medical procedures. More particularly, the application is related to devices and methods for occluding body lumens such as blood vessels.

BACKGROUND

Therapeutic embolization or occlusion of blood vessels may be used to treat a variety of vascular and non-vascular conditions including cerebral and peripheral aneurysms, ateriovenous malformation, uterine fibroids and various tumors. One commonly used agent for embolizing blood vessels is the embolic coil, a permanently implanted coiled wire structure which, when implanted into a blood vessel, occludes the vessel by causing thrombosis where it is deployed. Embolic coils may have different lengths and/or cross-sectional diameters, in order to fit into and occlude vascular structures of varying sizes. In use, the coils are delivered through a microcatheter in a narrow-diameter elongated configuration (e.g. to fit within a 3 Fr (or 1 mm diameter) catheter lumen). Once deployed into the vessel, the coil may assume a complex 3-D shape such as a helix, a spiral, a J-shape, or a birds-nest shape, and may include thrombogenic fibers or bundles of fibers along its length. Embolic coils are highly flexible, and can be delivered through narrow or tortuous vascular structures, but when occlusion of relatively vascular structures is desired, multiple coils may be necessary to achieve full occlusion, which in turn may increase the time and cost required for a therapeutic embolization procedure.

Another common occlusive agent is the occlusion plug, typically a braided structure comprising multiple strands of a shape memory material, most often nitinol. The occlusion plug, like the embolic coil, is capable of collapsing to a narrow diameter (for example to fit within the lumen of a delivery catheter) and then expanding to a relatively larger diameter which occludes the vessel of interest, but a typical plug generally occupies a larger volume and expands to a larger diameter than a typical embolic coil. This increased size allows occlusion plugs to efficiently occlude large-gauge vessels and vascular structures. In addition, occlusion plug procedures are generally less expensive, per-unit, than embolic coils, owing to the lower cost of materials for plug procedures (which typically require only a single device) versus coils (which may require implantation of multiple coils). However, due to their larger size, occlusion plugs are generally not able to be delivered through tortuous vascular structures, and typically require larger-bore catheters (e.g. 5-8 Fr, or 1.667-2.667 mm diameter) for delivery.

SUMMARY OF THE INVENTION

The present invention marries the superior deliverability of embolic coils with the superior occlusion of larger vascular structures that characterizes occlusion plugs.

In one aspect, the present invention relates to an occlusive device comprising a single elongate member which can be straightened out into a first configuration that allows the device to fit within the lumen of a microcatheter. When unconstrained, the wire assumes a second, deployed configuration characterized by a spiraling shape defining a space which is, variously, ovoid, spherical, and/or funnel-shaped and which can be symmetrical or asymmetrical. In various embodiments, the occlusive device includes a plurality of polymer fibers attached to the elongate member, optionally by means of a polymer sleeve, which polymer sleeve may include a radiopaque material. The fibers are, optionally, secured so that each fiber has a free end. In various embodiments, the elongate member is a nitinol wire and the plug includes a platinum band. The occlusive device also optionally includes a radiopaque marker.

In another aspect, the present invention relates to a system for treating a patient, which system includes a catheter and an occlusive plug as described above. In some cases, the inner diameter of the catheter is not more than about two times the outer diameter of the elongate member itself. The occlusive plug includes a single elongate member which can be straightened out into a first configuration that allows the device to fit within the lumen of a microcatheter. When unconstrained, the wire assumes a second, deployed configuration characterized by a spiraling shape defining a space which is, variously, ovoid, spherical, and/or funnel-shaped and which can be symmetrical or asymmetrical. In various embodiments, the occlusive plug includes a plurality of polymer fibers attached to the elongate member, optionally by means of a polymer sleeve, which polymer sleeve may include a radiopaque material. The fibers are, optionally, secured so that each fiber has a free end. In various embodiments, the elongate member is a nitinol wire and the plug includes a platinum band. The occlusive device also optionally includes a radiopaque marker.

In still another aspect, the present invention relates to a method of treating a patient that includes inserting a catheter into the vasculature of a patient and delivering an occlusive plug as described above. The occlusive plug may be delivered in a substantially linear elongated configuration, and may assume the spiraling shape defining an ovoid, spherical, funnel-shaped or other space when deposited within the vasculature at the desired site. In some cases, one or more embolic coils may disposed within the space defined by the plug.

DRAWINGS

Aspects of the invention are described below with reference to the following drawings in which like numerals reference like elements, and wherein:

FIG. 1, panels A, B, and C depicts several views of an exemplary occlusion plug in its deployed, expanded configuration. DIM A refers to the outer diameter of the deployed coil, while DIM B refers to its length.

Figure 2:
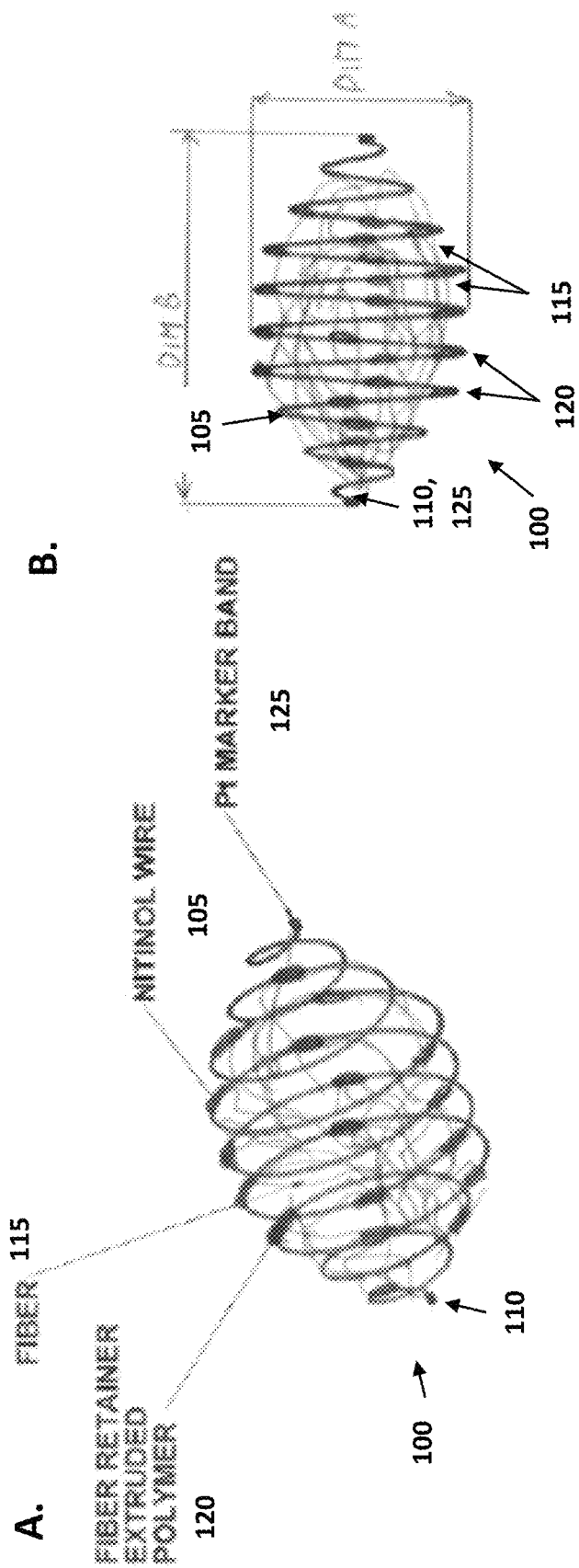

FIG. 2, panels A-B depicts several views of an exemplary occlusion plug which includes marker bands and polymer sleeves for retaining fibers.

Unless otherwise provided in the following specification, the drawings are not necessarily to scale, with emphasis being placed on illustration of the principles of the invention.

DETAILED DESCRIPTION OF THE PREFERRED EMBODIMENTS

In general, an occlusion plug according to the various embodiments of the present invention includes a single wire which, when unconstrained, assumes a programmed shape characterized by an outer diameter and a length which permit the plug to occlude a blood vessel.

Referring to FIG. 1A-B, an exemplary occlusion plug 100 according to the present invention includes a single elongate member 105. The elongate member 105, when unconstrained, assumes a spiraling shape (referred to as the "deployed configuration") characterized by a maximal diameter ("DIM A") which may range, in preferred embodiments from 3-22 mm for use in a variety of vessel diameters, and a length ("DIM B") ranging from 6 to 18 mm, depending on the size of the blood vessel or vascular feature to be occluded. The plug 100 optionally includes an atraumatic tip 110 at each end, and includes one or more fibers 115 which are connected to the elongate member 105.

Elongate member 105 is generally a wire, though it may be a wire-like structure such as a braided wire, a ribbon, etc. if such structure is suitable for the chosen application. The elongate member 105 is preferably formed of nitinol, which has shape memory and fatigue-resistance properties that are well suited to use in occlusion plugs according to the present invention. The elongate member 105 is manufactured to assume the deployed configuration by wrapping it around a structure that supports it in the deployed configuration (e.g. a mandrel having a complex shape complementary to the deployed configuration), then heat-setting the elongate member at a temperature above the fixing temperature of the material used to form the elongate member 105 (e.g. heating to a temperature above the fixing temperature of nitinol).

In its deployed configuration, the occlusion plug 100 has a shape which is useful for occluding a body lumen, such as a funnel shape, a substantially spherical shape, an ovoid shape, etc. and may be symmetrical or asymmetrical.

The fiber or fibers 115 are secured to the elongate member 105 using any suitable means. For example, in various embodiments of the present invention, the fibers 115 are wound or knotted around the elongate member. In other embodiments, such as the one illustrated in FIG. 2A-B, the fibers are secured by one or more polymer sleeves 120. The sleeve(s) 120 are, in preferred embodiments, formed as an extruded polymer tube which are attached to the elongate member 105 by heat-shrinking.

The occlusion plug 100 also includes, in preferred embodiments, one or more radiopaque markers such as Pt marker bands 125, to facilitate the visualization of the plug 100 under fluoroscopic or x-ray imaging. In the embodiment of FIG. 2A, the marker band 125 is disposed at each end of the elongate member 105, and may be integrated into or may comprise the atraumatic end 110.

In use, an occlusion plug 100 is deployed into a patient via a delivery catheter; the elongate member 105 is inserted into the lumen of the delivery catheter in an elongated configuration, permitting its insertion into and through catheters having very narrow inner diameters. When the distal end of the catheter is positioned near the site where the occlusion plug 100 is to be deployed, it is pushed through the distal opening of the catheter, where it expands and assumes its deployed configuration. The plug 100 preferably has a maximum outer diameter that is slightly larger than the inner diameter of the vascular structure into which the plug is placed, so that it exerts a radial force on the inner wall of the vascular structure which aids in its retention. During deployment of the plug 100, a user may visualize the vascular structure, delivery catheter, and plug under fluoroscopy, and may verify the correct placement and expansion of the plug 100 by reference to the marker bands 125.

Occlusion plugs 100 according to the present invention can be used for any vascular structure, but are particularly well suited to occlusion of the internal iliac artery, for instance as part of a procedure to harvest an endograft. Plugs of the invention can also be used in concert with embolic coils in order to achieve improved occlusions which are robust to recanalization. In one example, an occlusion plug 100 is placed into a vascular structure to be occluded, then one or more embolic coils are positioned within the space defined within the interior of the deployed plug.

Occlusion plugs according to the various embodiments of the invention have a number of advantages relative to currently marketed occlusion plugs. Among others is the extremely low profile of the plugs in their elongated or delivery configurations, which may be sized to fit within 3, 4, 5, 6, etc. Fr (i.e. 1, 1.33, 1.66, 2 mm) catheters, or even small catheters in some instances. It will be appreciated by those skilled in the art that these plugs can be deployed through narrower-gauge catheters than are currently used to deploy occlusion plugs. This in turn means that occlusion plugs of the present invention can be delivered through and into tortuous vascular structures not currently treatable using current plugs. In addition, plugs of the present invention utilize fibers which are anchored to the elongate member at a single point, allowing them to move within the blood flow and offering improved thrombogenesis relative to the fixed, braided cross-members which characterize currently marketed devices such as the Amplatzer™ series of occlusive plugs marketed by St. Jude Medical (St. Paul, Minn.).

At the same time, occlusion plugs of the present invention have advantages over currently used embolic coils, including lower cost due to the use of shape memory materials such as nitinol which are less expensive than the platinum used in many embolic coils today. Additionally, occlusion plugs according to the present invention can be used, by themselves, to occlude vascular structures that are too large to be occluded by a single embolic coil.

The examples presented above have focused on occlusion plugs which can be delivered as substantially linear lengths of coil through microcatheters into body lumens. In these embodiments, the outer diameter of the wire used to form the occlusion plug is closely matched to the inner diameter of the microcatheter. For instance, in one case, the wire has an outer diameter of ~0.0012 inches (0.03 mm), while the microcatheter has an inner diameter of 0.0021 inches (0.05 mm), limiting the degree to which the wire can coil within the catheter. In alternate embodiments, however, some coiling of the wire is allowable or even desirable. For instance, in one embodiment, the plug is formed of a tightly coiled wire, which is delivered through a microcatheter and assumes a secondary coiled shape as described above.

Finally, while the examples presented above have focused on occlusive plugs, and systems and methods utilizing such plugs, for vascular occlusion, those skilled in the art will recognize that plugs, systems and methods of the present invention can be used to occlude any body lumen amenable to therapeutic occlusion, including without limitation the fallopian tube.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. The term "substantially linear" is used in this specification to describe an arrangement that is at least partially "straightened out," for instance, as a wire, ribbon, fiber or other elongated, flexible body may become straightened out when placed under tension. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. An occlusive plug, comprising:
    a single elongate member comprising a shape-memory wire, the elongate member being configured to assume a spiraling shape defining an ovoid space when deposited within a body lumen;
    a plurality of polymer fibers, each of the plurality of polymer fibers having a first end attached to the elongate member and a free second end opposite the first end; and
    at least one polymer sleeve disposed about a circumference of the wire along a portion of a length of the elongate member and securing at least one of the plurality of polymer fibers to the elongate member.

2. The occlusive plug of claim 1, wherein the polymer sleeve includes a radiopaque material.

3. The occlusive plug of claim 1, wherein the wire is a nitinol wire.

4. The occlusive plug of claim 1, further comprising at least one platinum band.

5. The occlusive plug of claim 1, wherein the plurality of polymer fibers are attached to the elongate member at a single point.

6. The occlusive plug of claim 1, wherein the at least one polymer sleeve is an extruded polymer tube.

7. The occlusive plug of claim 1, wherein at least one of the plurality of polymer fibers is secured to the elongate member by a heat-shrunk polymer sleeve of the at least one polymer sleeve.

8. A system for occluding a body lumen, the system comprising:
    a delivery catheter having proximal and distal ends and a lumen extending therebetween; and
    an occlusive plug, comprising:
        a single elongate member comprising a shape-memory wire, the elongate member being configured to assume a first, elongate shape when fully inserted into the lumen of the catheter and to assume a second spiraling shape defining an ovoid space when deployed within the body lumen;
        a plurality of polymer fibers, each of the plurality of polymer fibers having a first end attached to the elongate member and a free second end opposite the first end; and
        at least one polymer sleeve disposed about a circumference of the wire along a portion of a length of the elongate member and securing at least one of the plurality of polymer fibers to the elongate member.

9. The system of claim 8, wherein an interior diameter of the catheter is not more than two times an outer diameter of the elongate member.

10. The system of claim 8, wherein the wire is a nitinol wire.

11. The occlusive plug of claim 8, wherein the polymer sleeve includes a radiopaque material.

12. The occlusive plug of claim 8, wherein the plurality of polymer fibers are attached to the elongate member at a single point.

13. The occlusive plug of claim 8, wherein the at least one polymer sleeve is an extruded polymer tube.

14. The occlusive plug of claim 8, wherein at least one of the plurality of polymer fibers is secured to the elongate member by a heat-shrunk polymer sleeve of the at least one polymer sleeve.

15. An occlusive plug, comprising:
    a single elongate member comprising a shape-memory wire, the elongate member defining an ovoid space with a longitudinal axis therethrough, and assuming a spiraling shape about the ovoid space along the longitudinal axis, when deployed within a body lumen;
    a plurality of polymer fibers, each of the plurality of polymer fibers having a first end attached to the elongate member and a free second end opposite the first end; and
    at least one polymer sleeve disposed about a circumference of the wire along a portion of a length of the elongate member and securing at least one of the plurality of polymer fibers to the elongate member.

16. The occlusive plug of claim 15, wherein the polymer sleeve includes a radiopaque material.

17. The occlusive plug of claim 15, wherein the wire is a nitinol wire.

18. The occlusive plug of claim 15, further comprising at least one platinum band.

19. The occlusive plug of claim 15, wherein the plurality of polymer fibers are attached to the elongate member at a single point.

20. The occlusive plug of claim 15, wherein the at least one polymer sleeve is an extruded polymer tube.

* * * * *